(12) United States Patent
Plüss

(10) Patent No.: US 6,270,658 B1
(45) Date of Patent: Aug. 7, 2001

(54) DRINKING WATER SUPPLY APPARATUS

(75) Inventor: Heinz Plüss, Schönbühl (CH)

(73) Assignee: Digmesa AG, Ipsach ( * ) Notice: Subject to any disclaimer, the term of this patent is extended or adjusted under 35 U.S.C. 154(b) by 0 days.

(21) Appl. No.: 09/063,783

(22) Filed: Apr. 22, 1998

(30) Foreign Application Priority Data

Apr. 23, 1997 (DE) .............................................. 197 17 009

(51) Int. Cl.$^7$ ...................................................... C02F 9/00
(52) U.S. Cl. ............................ 210/98; 210/104; 210/143; 210/195.1; 210/196; 210/202; 210/257.1; 210/258; 210/259; 210/416.3
(58) Field of Search .................................... 210/668, 764, 210/805, 98, 104, 195.1, 196, 202, 257.1, 258, 259, 266, 143, 416.3

(56) References Cited

U.S. PATENT DOCUMENTS 4,317,733 * 3/1982 Xhonneux ............................. 210/764
4,328,830 * 5/1982 Greer ................................. 137/625.4
5,873,996 * 2/1999 Rozelle et al. ..................... 210/257.1

* cited by examiner

Primary Examiner—Ivars Cintins
(74) Attorney, Agent, or Firm—Antonelli, Terry, Stout & Kraus, LLP

(57) ABSTRACT

To bring maximum sterility in a stationary drinking water supply installation with a water tank, the invention provides a method for filling a drinking water installation in which, after filling a tank with fresh water, the water is circulated at least over a filter. The invention also provides an apparatus for drinking water supply from a drinking water tank with a supply pipe connectable to a fresh water source and which has a three-way valve (6) with an inlet (4) connected to the fresh water intake (3), as well as a second inlet (22) and a supply pipe (5) leading to the tank (2). There is also a return pipe (21) leading from the water tank (2) to the second inlet (22) of the three-way valve (6) and a circulating pump (9) in the water circuit formed by the return pipe (21) and supply pipe (5).

3 Claims, 1 Drawing Sheet

DRINKING WATER SUPPLY APPARATUS

FIELD OF THE INVENTION

The invention relates to a method for filling a drinking water installation, which has a fresh water supply pipe and a water tank receiving the drinking water, in which the water is filtered through a filter and is provided with silver ions by a silver ion admixing unit, as well as an apparatus for supplying drinking water from a drinking water tank with a supply pipe connectable to a fresh water source and which contains a filter and a silver ion admixing unit.

BACKGROUND OF THE INVENTION

In the case of mobile inhabitable units, such as ships, mobile homes and caravans, mobile drinking water installations are also provided. They have a water tank, which is filled at a stationary water source and then, during the movement of the unit and independently of stationary water sources, is available for drinking water supply purposes. For stabilizing the drinking water quality and in particular to avoid bacteria, it is known to add silver ions to the water. It is also-appropriate to filter the water supplied to the mobile tank, in order to remove pollutants before the water enters the tank.

It has now been found that such a filter with the residual water therein can be highly contaminated, even if silver ions are added to the water in the water tank. On refilling, said highly contaminated water is rinsed out of the filter into the water tank and cannot be restored to a satisfactory state even when provided with silver ions. It has in particular an extremely unpleasant smell. This deficiency has also not been eliminatable by an additional activated carbon filter. However, it is not recommended to carry out silver ion admixing prior to flowing through the filter, because to a significant extent the silver ions are filtered out in the filter and therefore greatly reduce the effectiveness of silver ion admixing with respect to the silver ions contained in the water in the tank, i.e. the efficiency of silver ion admixing is reduced.

Thus, whilst ensuring a high efficiency of silver ion admixing in a mobile drinking water supply installation, the problem of the invention is to prevent contamination of the water still in the supply pipe to the water tank and more particularly also in the filter.

SUMMARY OF THE INVENTION

According to the invention, this problem is solved with a method of the aforementioned type and which is characterized in that, after filling the tank with fresh water, the water is circulated at least over the filter. For solving the problem the invention also provides an apparatus of the aforementioned type, which is characterized by a three-way valve with an inlet connected to the fresh water intake, as well as a second inlet and a supply pipe leading to the tank, by a return pipe leading from the water tank to the second inlet of the three-way valve and by a circulating pump in the water cycle formed by the return pipe and the supply pipe.

Due to the fact that, after filling, the fresh water in the tank and provided with silver ions is again circulated through the entire pipe system and in particular also the filter, it is ensured that throughout the pipe system and in particular the filter water provided with silver ions is present and therefore in addition to the tank the entire pipe system, including the filter, is protected against contamination. Although in the case of the inventive design of the apparatus, the silver ion admixing unit could fundamentally be positioned upstream of the filter, in order to increase and secure the effectiveness of the silver ion admixing, it is generally positioned in the flow direction behind or downstream of the filter and preferably immediately in front or upstream of the tank, so that according to a preferred development of the inventive method, the circulated water is firstly pumped through the filter and then the silver ion admixing unit.

In preferred manner, the method is further developed in that the water of the water tank is passed by means of a three-way valve into the fresh water supply pipe and that a three-way valve located in the supply pipe, after filling the water tank, is switched by a connection connectable to the fresh water pipe to a circulating pipe leading from the water tank to the three-way valve and a circulating pump is put into operation.

Thus, after the filling of the tank and reaching a maximum filling level, an automatic circulation is brought about ensuring that always and in all cases following filling a circulation takes place, without any need for additional operating processes, which could be forgotten.

According to a further development of the apparatus according to the invention, the pump is located in the supply pipe. According to another preferred development, in the pipe containing the silver ion admixing unit is provided a flow meter, by means of which the silver ion delivery rate of the silver ion admixing unit can be controlled as a function of the flow rate. An overfilling of the tank or an emptying without prior warning can be prevented by providing the water tank with level sensors. On dropping below a predetermined minimum level, a corresponding level sensor can emit a warning signal. On reaching the maximum level an automatic separation of the inventive apparatus from the stationary water supply can take place, in that the inlet of the three-way valve to the stationary water supply is closed and optionally, simultaneously, there is a switching over to the return pipe, i.e. the opening of the three-way valve inlet connected thereto. In principle, filling can also be ended before reaching the maximum filling level. Here again the three-way valve is switched over for circulation purposes. In an extremely preferred development a control device is provided for switching over the three-way valve and optionally a subsequent connecting in of the pump on reaching the maximum filling level in the water tank. A very short time is adequate for circulation purposes, e.g. less than 60 seconds. As a result of the invention, the complete installation or water-carrying parts are filled with silver ion-treated water and water contamination is avoided.

BRIEF DESCRIPTION OF THE DRAWING

Further advantages and features of the invention can be gathered from the claims and the following description of an embodiment of the invention and with reference to the attached single drawing showing the preferred embodiment of the apparatus according to the invention in diagrammatic form.

DETAILED DESCRIPTION OF THE DRAWING

Figure 1:
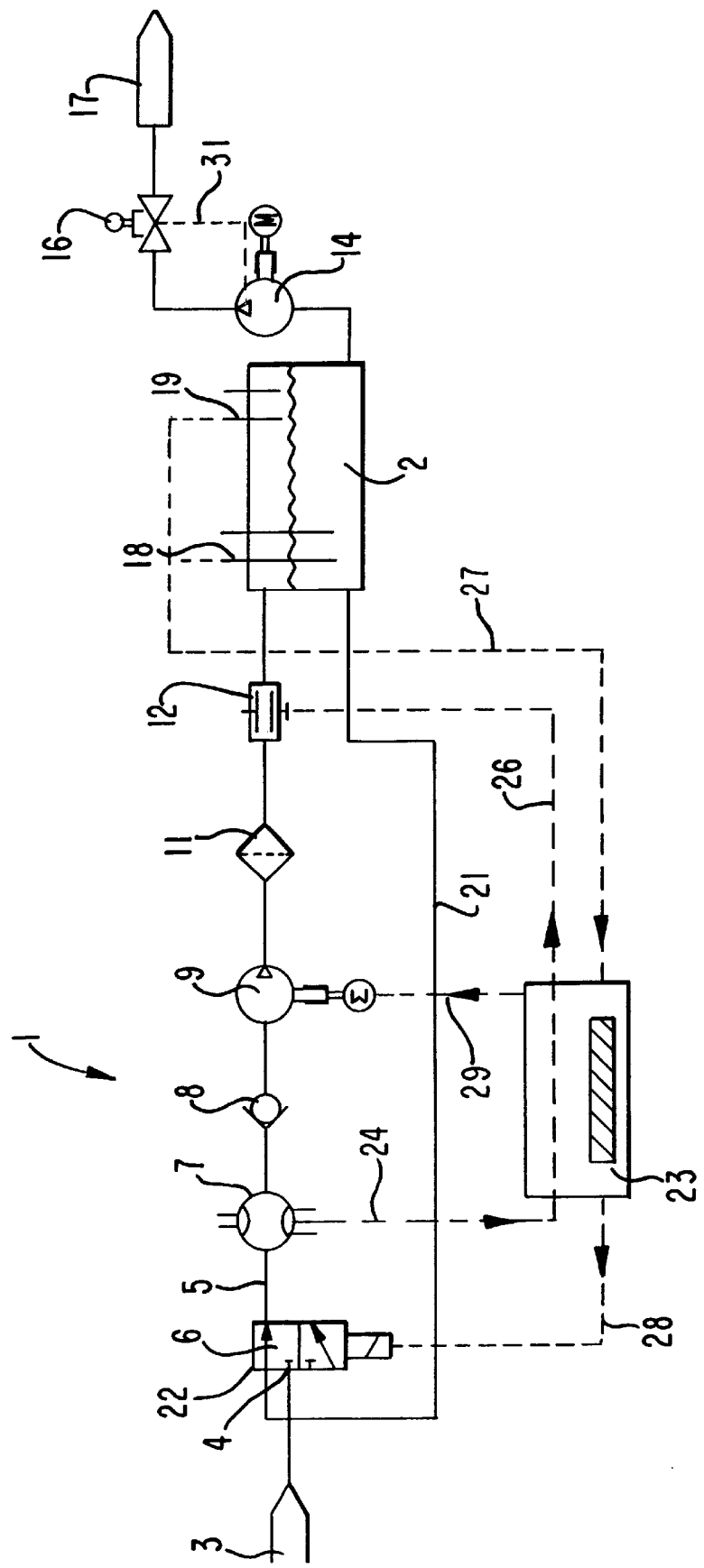

The apparatus 1 according to the invention for drinking water supply from a drinking water tank 2, in which the latter is supplied with fresh water by means of a drinking water intake 3, the inlet 4 of a three-way valve 6 and a supply pipe 5, contains the following parts in the indicated order: flowmeter 7, check valve 8, circulating pump 9, filter 11 and silver ion admixing unit 12. From the drinking water tank 2 an outflow pipe 13 leads via an extraction pump 14 and an extraction water tap or faucet 16 to a water outlet 17. The tank 2 contains two level sensors 18, 19 for establishing the maximum and minimum filling level in the water tank 2.

From the water tank 2 a return pipe 21 leads to a second inlet 22 of the three-way valve 6. The apparatus 1 according to the invention also has a control device 23. From the flowmeter 7 a flow measuring pipe 24 leads to the control device 23 and from the latter a flow control pipe 26 passes to the silver ion admixing unit 12. In addition, a level measuring pipe 27 leads from the level sensors 18, 19 to the control device 23, from which a valve control pipe 28 and a pump control pipe 29 lead to the three-way valve 6 or pump 9. Finally an extraction pump control pipe 31 passes from the extraction water faucet 16 to the extraction pump 14, which could also pass via the control device 23.

For filling the water tank 2, the apparatus according to the invention is connected by means of the fresh water intake 4 to a stationary fresh water supply installation. Under the intrinsic pressure of the fresh water supply installation, when the circulating pump 9 is idling, or also when the circulating pump 9 is activated, fresh water is supplied through the supply pipe 5 and the elements located therein to the fresh water tank 2 until the maximum level sensor 19 delivers a corresponding filling signal, via the level measuring pipe 27 to the control device 23. The latter then closes the inlet 4 of the three-way valve 6 and opens the inlet 22 via the control pipe 28 and optionally starts the pump 9 by means of the control pipe 29. The pump circulates the water in the tank 2 and pipe system through the latter. During the water flow through the pipe 5 and consequently the flowmeter 7, independently of whether fresh water is supplied or water is circulated in the aforementioned manner, the flowmeter 7 measures the flow and delivers a corresponding flow measurement signal via the measuring pipe 24. As a function of the flow measuring signal, the silver ion admixing unit 12, by means of the control pipe 26, is supplied with a flow adapted to the water through-flow, so that silver ions from the silver ion admixing unit 12 are delivered into the flowing through water in flow-dependent and therefore accurately dosed manner. In order to bring about a regular removal of the silver lamellas in said unit, at certain intervals the control unit 23 brings about a polarity reversal with respect to the electrodes. The circulation of the water takes place over a predetermined, short time of 30 to 60 seconds.

As a result of the invention, all the water in the water supply apparatus 1 and not only the water in the tank, but also in particular the water in the supply pipe 5 and especially in the filter 11 is treated with silver ions, which avoids contamination of the water, particularly in the filter 11.

For extracting or removing water from the water tank 2, the faucet 16 is opened, which puts the extraction pump 14 into operation and pumps water out of the water tank 2 and leads it to the outlet 17. If the water level in the water tank 2 has dropped to such an extent that the level sensor 18 responds, the latter emits a corresponding signal to the control unit 23, which then generates an acoustic and/or optical warning signal, which indicates the need to refill the water tank 2.

What is claimed is:

1. Moveable apparatus for drinking water supply, said apparatus comprising a drinking water tank, a supply pipe connected to said tank, a three-way valve connected to said supply pipe leading to said tank, said valve having first and second inlets, said first inlet being connected to a fresh water intake connectable to a fresh water source, a return pipe connected to said tank and leading back from said water tank to said second inlet of said valve, a circulating pump in the water circuit formed by said return pipe and said supply pipe, a filter provided in said supply pipe, a silver ion admixing unit provided in said supply pipe downstream of said filter, a flow meter provided in said supply pipe by means of which it is possible to control the silver ion delivery rate of the silver ion admixing unit as a function of the flow rate, and a control device for switching over said three-way valve for closing said first inlet and opening said second inlet of said valve and subsequent connecting in of said circulating pump on reaching a maximum filling level in the water tank.

2. Apparatus according to claim 1, wherein the pump is provided in the supply pipe.

3. Apparatus according to claim 1, wherein the water tank is provided with level sensors.

* * * * *